US008945931B2

(12) United States Patent
Agrawal et al.

(10) Patent No.: US 8,945,931 B2
(45) Date of Patent: Feb. 3, 2015

(54) METHOD AND KITS TO DETECT BERYLLIUM BY FLUORESCENCE

(75) Inventors: Anoop Agrawal, Tucson, AZ (US); John P. Cronin, Tucson, AZ (US); Alan G. Goodyear, Tucson, AZ (US); Juan Carlos Lopez Tonazzi, Tucson, AZ (US)

(73) Assignee: Berylliant, Inc., Tucson, AZ (US)

( * ) Notice: Subject to any disclaimer, the term of this patent is extended or adjusted under 35 U.S.C. 154(b) by 1375 days.

(21) Appl. No.: 11/152,620

(22) Filed: Jun. 14, 2005

(65) Prior Publication Data

US 2005/0280816 A1   Dec. 22, 2005

Related U.S. Application Data

(60) Provisional application No. 60/581,234, filed on Jun. 18, 2004.

(51) Int. Cl.
  *G01N 33/20* (2006.01)
  *G01N 21/64* (2006.01)
  *G01N 21/94* (2006.01)
  *G01N 21/77* (2006.01)

(52) U.S. Cl.
  CPC ............ *G01N 21/643* (2013.01); *G01N 21/94* (2013.01); *G01N 2021/7786* (2013.01)
  USPC ........................................................ 436/79

(58) Field of Classification Search
  CPC ...... G01N 33/20; G01N 33/24; G01N 21/643
  USPC ........................................................ 436/79
  See application file for complete search history.

(56) References Cited

U.S. PATENT DOCUMENTS

| 4,455,741 | A  | * | 6/1984  | Kolodner .................. 438/16 |
| 5,190,666 | A  | * | 3/1993  | Bisconte .................. 210/744 |
| 7,129,093 | B2 | * | 10/2006 | McCleskey et al. ........... 436/79 |

OTHER PUBLICATIONS

U.S. Appl. No. 10/812,444.
Matsumiya, H., Hoshino, H., Yotsuyanagi, T., "A novel fluorescence reagent, 10-hydroxybenzo[h]quinoline-7-sulfonate, for selective determination of beryllium(II) ion at pg cm$^{-3}$ levels." *Analyst*, vol. 126, pp. 2082-2086 (2001).
Edel M. Minogue, Deborah S. Ehler, Anthony K. Burrell, T. Mark McCleskey, Tammy P. Taylor, "Development of a New Standard Method for the Detection of Beryllium on Surfaces,", Oct. 2005.
Kevin Ashley, T. Mark McCleskey, Michael J. Brisson, Gordon Goodyear, John Cronin and Anoop Agrawal, "Interlaboratory Evaluation of a Portable Fluorescence Method for the Measurement of Trace Beryllium in the Workplace,", Oct. 2005.
Baron, P.A., "Factors Affecting Aerosol Sampling", Chapter 0, NIOSH Manual of Analytical Standards, Mar. 15, 2003, National Institute of Occupational Safety and Health, USA.

* cited by examiner

*Primary Examiner* — Paul Hyun

(57) ABSTRACT

A low-cost practical method of determining beryllium or a beryllium compound thereof in a sample is disclosed by measuring fluorescence. This method discloses optical filters for use with low cost fluorometers which may be used to quantitatively determine the presence of beryllium. This method may be extended to estimate particle size distribution for particles comprising Beryllium. A method is also disclosed to store solutions for extended period of time so that these materials are stable during transportation and in the labs.

2 Claims, 8 Drawing Sheets

US 8,945,931 B2

METHOD AND KITS TO DETECT BERYLLIUM BY FLUORESCENCE

RELATED APPLICATION/CLAIM OF PRIORITY

This Application is related to and claims priority from Provisional Application Ser. No. 60/581,234, filed Jun. 18, 2004, entitled Method and Kits to Detect Beryllium by Fluorescence, which provisional application is incorporated by reference herein.

FIELD OF THE INVENTION

The present invention relates to the detection and quantification of beryllium by fluorescence. More particularly, the present invention relates to the detection and quantification of beryllium in a way so that low-cost kits may be designed to address the issue.

BACKGROUND OF THE INVENTION

Beryllium is a metal that is used in a wide variety of industries including electronics, aerospace, defense, and the Department of Energy (DOE) complex. Exposure to beryllium containing particles can lead to a lung disease called Chronic Beryllium Disease (CBD). CBD involves an uncontrolled immune response in the lungs that can lead to deterioration in breathing capacity and ultimately death. It is clear that even in processes where beryllium dust has been controlled to very low levels, cases of disease still persist. In fact, there have been cases of CBD reported in people that have had no obvious direct contact with beryllium operations. Despite the fact that very low exposure levels can lead to CBD, the onset of disease can take decades.

Recent new regulations from DOE dictate a permissible exposure limit of 0.2 $\mu g/m^3$ in air, a housekeeping level of 3 $\mu g/100\ cm^2$ on a surface, and a release level for materials after beryllium exposure where the surface contamination due to beryllium must not exceed 0.2 $\mu g/100\ cm^2$. There is a discussion in the beryllium community if the permissible air exposure limit needs to be lowered to 0.02 $\mu g/m^3$. Currently, thousands of surface wipes and air filters are analyzed annually for beryllium. In addition OSHA has detected airborne levels of beryllium at numerous sites within the United States. The present technique for detecting beryllium is a surface analysis that involves wiping an area with a filter paper, performing a microwave digestion with acid to dissolute beryllium or its compounds, and then analyze by inductively coupled plasma (ICP) atomic emission spectroscopy (AES). For analyzing airborne samples, one draws a known quantity of air through a filtering medium and then it is treated in a similar fashion to the surface wipes. This process can take two days or more and is not readily usable in the field. The ICP-AES technique also requires highly trained operators and the entire sample is consumed in order to meet the detection levels so that a sample that is identified as positive for beryllium cannot be checked or verified with a second run.

Although there are several reports of being able to detect beryllium with a fluorescent indicator (see Matsumiya), only recently quantitative fluorometric beryllium detection methods that have been shown to be effective for the current exposure regulations. Three key elements to a useful detection system that have been missing previously are: first, the detection system must be capable of dissolving both beryllium oxide and beryllium metal; second, the detection system must work in the presence of other metals and fluoride ions. Third, the detection system must be easy to use and preferably offer the ability to be field portable. Most fluorescent indicators reported in literature do not tolerate the presence of fluoride ions, which is critical if a fluoride-based medium is used to dissolve the beryllium. The few reports of fluorescent indicators that can tolerate fluorides, have used complicated procedures involving heating with acid for dissolution and a titration process to obtain the final pH that require long periods of time and prohibit use in the field.

The extensive chemistry required in previous fluorescent systems and interferences from other metals have limited their use, and to date there is no simple approach to beryllium detection by fluorescence. A quick, simple and specific approach has now been developed for the detection and quantification of beryllium as claimed in U.S. patent application Ser. No. 10/812,444 filed on Mar. 30, 2004 and is incorporated herein by reference. Further this method provides a quantitative method of determining beryllium or a compound thereof (including beryllium oxide) in a sample, which has a fast turnaround time and can be made to be readily field portable.

One object of the present invention is to practically enable the method by prolonging the shelf life of the indicator so that practical test kits may be designed which are durable.

Yet another objective of this invention is to use this method to get a particle size distribution of beryllium comprising particles which are airborne.

Another objective of this invention is to increase the sensitivity of the test by tuning the chemistry of the process and thermal control of the sample being measured, in addition it is also beneficial to extend the dynamic range of the measurement.

Yet another objective of this invention is to assist in the dissolution process by changing at least one of the chemistry of dissolution solution and/or influencing the kinetics of dissolution by heat, microwave and ultrasonic treatment for samples to be analyzed by fluorescence.

Another objective of the invention is to provide a highly automated system to analyze several samples with less handling and labor both to reduce cost and increase process safety and consistency.

SUMMARY OF THE INVENTION

In accordance with the purposes of the present invention, as embodied and broadly described herein, the present invention provides a method of determining the presence and amount of beryllium or a beryllium compound in a sample including admixing a sample suspected of containing beryllium or a beryllium compound with a dissolution solution for sufficient time whereby beryllium or a beryllium compound within said sample is dissolved, mixing a portion from the admixture with a buffered solution containing a fluorescent indicator capable of binding beryllium or a beryllium compound to the fluorescent indicator, and, determining the presence of an amount of beryllium or a beryllium compound within the sample by measuring fluorescence from the fluorescent indicator. For practical kits, particularly for use in the field, it is important that the dissolution solutions and the buffered detection solutions have a long shelf life so that these may be easily transported and stored for a length of time without deterioration or loss of their properties.

Further, it is preferred that a low cost instrument be used to detect the beryllium by fluorescence. It is further preferred that such an instrument be portable. It has been found that with proper selection of optical filters on these instruments, the low cost detectors employing photomultiplier tubes and photosensors may be used for detection of fluorescence signals yielding sensitivity down to less than 1 part per billion, and more preferably below 100 parts per trillion.

Beryllium may be collected by wiping a surface suspected of being covered with beryllium particles and analyzing the wipe or by capturing particles on a filter as the air is passed through it. Alternately, beryllium may be monitored in the air by separating and collecting beryllium particles by passing the air over a series of meshes with decreasing mesh size and then analyzing the separated samples for beryllium. In both cases the wipe or the filter is first treated in the dissolution solution to extract beryllium (or its oxide). Particularly for air sampling, the beryllium particles may be separated based on their size and collected so that their analysis may yield a size distribution. Various methods of particle collection mechanisms will be listed which may be used with this technique.

DETAILED DESCRIPTION

Figure 1:
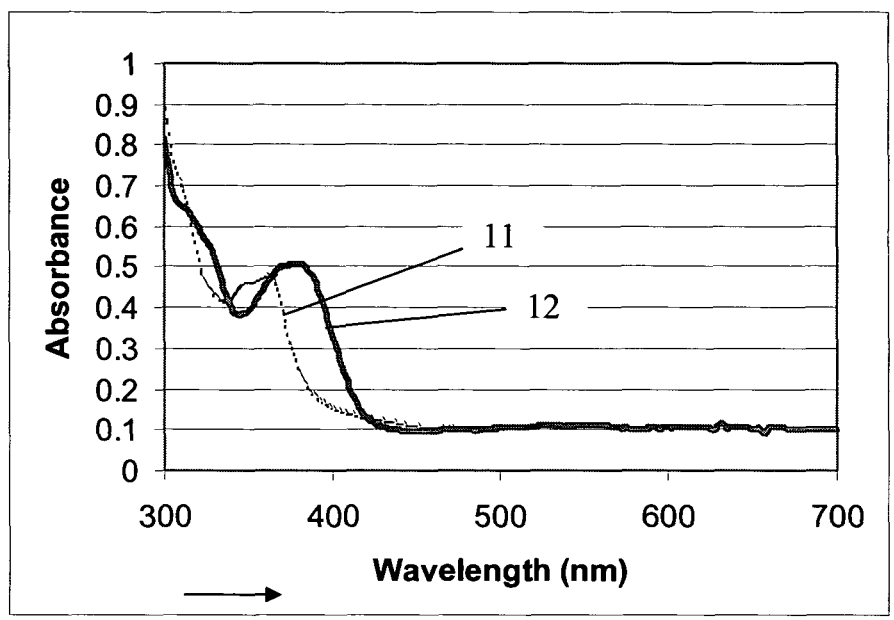
FIG. 1 shows absorption spectra of freshly prepared detection solution, with and without beryllium.

The present invention is concerned with the design of practical kits to determine the presence and amount of beryllium or a beryllium compound in a sample. Beryllium particles which pose health hazards may be collected in a number of ways. Beryllium may be collected by wiping a surface suspected of having beryllium particles and analyzing the wipe. Alternately, beryllium may be monitored in the air by collecting beryllium (or a compound comprising beryllium such as beryllium oxide) in a standard fashion over a media and then analyzing the filter for beryllium. In all cases the wipe or the media is first treated in the dissolution solution to extract beryllium Typically, 1250 to 2000 liters of air at a flow-rate of 1 to 4 liters/minute is used to collect particulates on the media. The media or the filter which has trapped beryllium particulates are analyzed for quantification. The air-sampling device may be a portable one being worn by a person or it may be mounted in a specific work area. Particularly for air sampling, the beryllium particles may be separated based on their size so that their distribution may be determined. Any method may be used to collect and separate beryllium particles, for example, air is drawn through a series of meshes with decreasing mesh size. Beryllium particles, if any, are thus separated based on their size and then collected. This collection may be on a media, such as a porous or filter paper or cloth which will capture these particles. Each of the fractions are then analyzed separately for beryllium quantification to obtain a distribution of mass of beryllium vs. particle size. This is important (see Baron) as it has been shown that the aerodynamic diameter of respirable particles is less than 10 microns, the ones that can pass through the thoracic gland is less than 30 microns and that it is possible to inhale particles larger than this size.

A variety of wipes and wiping methods may be used. For example ASTM D6966 describes methods on how to wipe in order to collect the particles efficiently. One may use dry wipes or wet wipes. Dry wipes may work better on softer surfaces as compared to the harder ones. The wetting medium for wet wipes may be aqueous or non-aqueous. Aqueous medium may have surfactants to change the surface tension in order to wet and capture the particles more efficiently. Surfactants may be ionic or non-ionic. Some of the surfactants are polyethylene and polypropylene glycols in various molecular weights as Triton™ available from Aldrich Chemical Company (Milwaukee, Wis.). Some examples of Triton™ are N-101 reduced, SP-135, SP-190, X-100, X-100 reduced, X-114, X-114 reduced, X-405 and X-405 reduced. Usually, the molecular weight of the glycols is lower than 5000 and preferably lower than 2000. Since these materials have high molecular weight, their vapor pressure is lower as compared to water, thus they do not have a tendency to dry out and may be used as by themselves as the wetting media. Non-drying wetting fluids may also leave stains on the surfaces which may take long to dry or require a clean-up later. The most preferred wetting media is water, or water comprising surfactants.

The wipe may comprise paper, cellulose, cellulose esters, nitrocellulose, acrylic, polyvinyl acetate, nylon, polyvinyl alcohol, polyester, polycarbonate, polytetrafluoroethylene, polyvinylidene fluoride, polyolefins, or any other media which serves the purpose of collection, easily releases captured particles in the dissolution solution and preferably does not disintegrate in the dissolution solution. These may be hydrophilic or hydrophobic. Those media which reproducibly perform from a collection perspective, have no metal impurities and are cost-effective are most preferred. To increase the efficiency of collection from dry or wet wipes their surfaces may be engineered so that pores are provided on their surfaces in the same size range as the expected particle sizes so as to firmly collect and lodge the particles. An example of such engineered surfaces may be filters made out of various materials (e.g. see 2005 Catalog from Fisher Scientific page 518 to page 529 (Pittsburgh, Pa.), or for example StretchN'Dust® from Chicopee (Mooresville, S.C.)). Another example of these are ash-less paper filters from Whatman (Haverhill, Mass.) type 541. Further it is preferred that the media is wetted before collecting the particles from the surface. It is also preferred that water in a pre-determined quantity is used for this purpose. As an example for filters 541 in a size of 47 mm in diameter (or 17.3 square cm in surface area), it has been found that wetting with about 200 microliters of water is sufficient. Generally the volume of wetting media is proportional to the surface area of the collection media, which should typically be in the range of 2 to 100 microliters of fluid per square cm of the media area. It is important that consistent amounts of wetting material be used, the surface wiped and wipe transferred to the dissolution tube solution immediately. This keeps the dilution of the dissolution solution by the wetting agent small and consistent. These media may also be used to collect sample from surfaces and air in other ways. For example micro-vacuuming may be used on a surface and particles collected on the media.

Beryllium and its compounds in liquid media such as water may also be analyzed by this method. If the beryllium is present as particulates then it may be filtered using the media (or filters) as described above, and then the filter is preferably dried and put in a dissolution tube. Alternatively for solutions, one may place predetermined amount of beryllium comprising solution on to a filter or the media described above, evaporate the solvent and subject the filter to the same dissolution process. Solutions including aqueous solutions are simply substituted for dissolution solution since these already have beryllium in solution.

The advantages of the process of the present invention include: a simple dissolution step that can dissolve beryllium oxide and beryllium metal in less than thirty minutes by agitation; tolerance of a wide variety of other metals and fluoride at large concentrations; the use of a final buffered solution to avoid titration, a fast turnaround time of less than one hour and the ability to be field portable. The dissolution technique involves preferable use of ammonium bifluoride as this rapidly dissolves several beryllium compounds including beryllium metal and beryllium oxide. Further, a buffered solution including the fluorescent indicator is used and is essential to fast detection that can be done in the field. It is preferred that the concentration of ammonium bifluoride be as low as needed for dissolution so that when it is mixed with the solution with the fluorescent indicator (detection solution), the pH is still high for strong fluorescent signal. Any concentration of the ammonium bifluoride solution may be used as long as the pH of the mixture of the two solutions is basic as discussed later.

As a preferred fluorescent indicator, 10-hydroxybenzo[h]quinoline-7-sulfonate (10-HBQS) is used. The buffered solution preferably includes a buffer having a pKa between about 7 and 13.5 and more preferably in excess of 12.5. A typical buffer that is preferred is an amine buffer and most preferably is an amino acid such as lysine. Any of the lysine compounds may be used, e.g., D-lysine, L-lysine, DL-lysine, their monochlorides and dihydrochlorides. A preferred lysine compound is L-lysine monohydrochloride. The solution may also contain aminocarboxylates such as ethylenediaminetetraaceticacid (EDTA), diethylenetriaminetetraacetic acid (DTTA), triethylenetetraminehexaacetic acid (TTHA), and the like, or salts thereof, as a chelating agent to bind metals other than beryllium. Preferred salts of EDTA are EDTA dipotassium dihydrate and EDTA disodium dihydrate. Other chelating agents such as aminophosphonates may be used as well. There are a few preferable choices of indicators, all of which are based on forming six-member rings with the beryllium ion bound to a phenolate oxygen and a pyridine nitrogen. The preferred indicator is 10-HBQS.

FIG. 1 shows the absorption spectra 11 of a preferred formulation of a detector solution. The solution was made by using 1.7 liters of de-ionized water (greater than or equal to 18 Mohms), 19.51 g of lysinemonohydrochloride, 1.99 g of EDTA disodium dihydrate, 0.0367 g of 10-HBQS and then titrating this with a solution of 2.5N sodium hydroxide to a final pH of 12.85. This figure also shows the absorption spectra 12 of the same solution but after adding beryllium at 20 ppm final concentration.

The method of the present invention involves obtaining a sample on a medium (such as on a filter paper by wiping a surface or capturing airborne particles) and then placing the medium into a vial and adding 5 mL to 100 ml of an aqueous ammonium bifluoride solution for dissolution of beryllium captured on the medium. A preferred concentration is one percent ammonium bifluoride solution which can dissolve up to 10 mg of either beryllium or beryllium oxide in less than 30 minutes with simple shaking. A mechanical shaker with a timer is preferred for consistency. Next, a predetermined quantity of the ammonium bifluoride solution (with dissoluted beryllium sample) is added to the a buffered indicator solution, containing a fluorescent indicator and a buffer, to neutralize the solution and bind beryllium ions to the fluorescent indicator. When 10-HBQS is used as the fluorescent indicator, fluorescence at 475 nm can be used to quantitatively determine the beryllium. The most remarkable aspect of this method is its ability to tolerate a wide range of potentially interfering metals at high concentrations. A wide variety of metals including iron, aluminum, and uranium at levels 10,000 times the beryllium concentration have been reported and have seen no interference in detecting the beryllium (see Minogue, et al, 2005).

Figure 2:
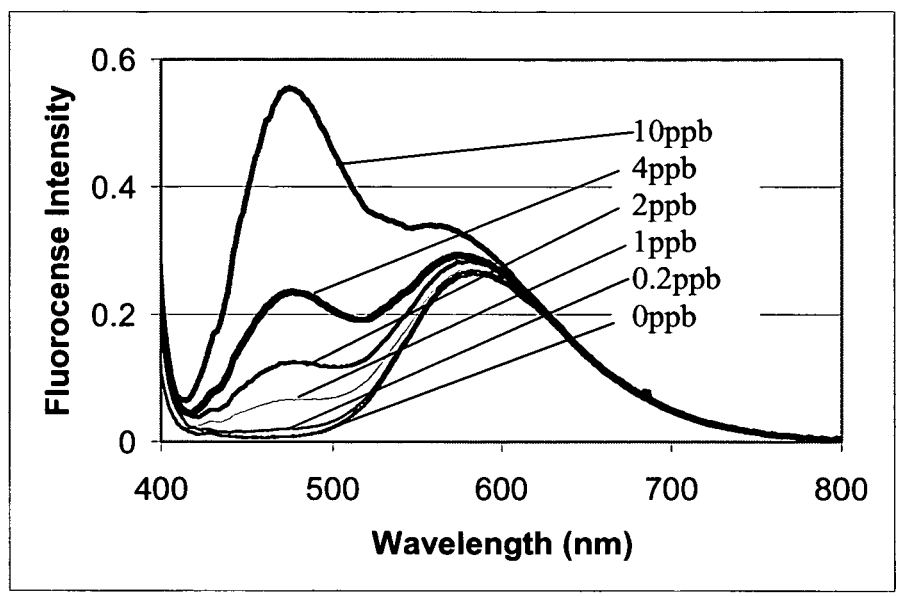
FIG. 2 Fluorescence spectra of detection solution with various concentrations of beryllium.

FIG. 2 shows the fluorescence spectra of the detector solution when it is mixed with various beryllium containing solutions. The broad peak at 475 nm is more sensitive to the lower beryllium concentrations, and the broad peak at 575 nm may be used for higher concentrations, as it is less sensitive with change in beryllium amount. The results from both may be simultaneously read and combined by the software so that the dynamic range of the instrument may be extended. A preferred dynamic range for quantification is between 0.01 to 10 μg of beryllium on the media, and a more preferred range is between 0.001 to 10 μg of beryllium on the media. This method has high flexibility to be tailored to any desired range.

In the prior art, the media is usually a filter paper (e.g., Whatman 541 for wipe and Mixed cellulose ester (MCE) filter for air sampling (see Minogue; Ashley and patent application Ser. No. 10/812,444) spiked with different amounts of beryllium compound and dissoluted with 5 ml of 1% ammonium bifluoride solution by mechanical agitation. A 0.1 ml of this solution was added to 1.9 ml of the preferred detection solution (described above in FIG. 1 and description) and then measured by fluorescence. Currently, this method determines between 0.014 μg and 4 μg per wipe or filter (media). This method is adequate to meet regulation standards where between 0.2 and 4 μg needs to be measured on a media (or a filter paper). Further, this method has the ability to verify a result by rerunning fluorescence or doing inductively coupled plasma atomic emission on the 4.9 mL of the dissolution solution that remains unused. However, if the regulations are changed in future to be able to reliably measure down to 0.02 μg on the media, then it would be preferred that the method detection limit is about 0.002 μg.

Further, the prior art method may be modified in novel ways to accommodate beryllium materials that are hard to dissolute, extend the range of measurement and extend its sensitivity to detect smaller quantities of beryllium. Many of these methods use modifications to the preferred chemistry of the dissolution and the detection solutions, whereas the others focus on instrument and measurement modifications or combine both of these types of modifications.

To increase the solubility kinetics of larger particles, particularly more refractive materials such as beryllium oxide, the dissolution solution may also comprised of acids and their mixtures, and acids mixed with ammonium bifluoride. One has to be careful that when the detection solution is mixed with the dissolution solution, the volumes used and the buffer capacity of the detection solution is such so that a high pH is maintained for the mixture. Typically pH of the mixture is in excess of 7 and more preferably in excess of 10 and most preferably in excess of 12. Some preferred acids are hydrochloric acid, sulfuric acid, hydrofluoric acid and nitric acid. Some of the preferred acid containing dissolution solutions are made in 1% acid solutions in water to which ammonium bifluoride is added so as to result in a final concentration of 1% as well, for example 1% ammonium bifluoride solution (weight: volume) in 1% hydrochloric acid solution. Further the dissolution process of beryllium and its compounds captured onto the wipe in these solutions is aided by mechanical shaking and/or agitation. One may also use heat, microwaves and ultrasonic vibrations to expedite or accelerate the process. Typically the preferred temperatures are lower than 100° C., e.g., 75° C., the preferred microwave frequencies are 915 MHz and 2450 MHz and the preferred ultrasonic frequencies are in the range of 18 kHz to 300 kHz. The dissolution time for a fixed chemistry depends on the chemistry of the dissolution solution and the particles, particle size (e.g., surface area) and the type of acceleration factor chosen as listed above. It is desirable to select a shortest period for dissolution, preferably less than 60 minutes to ensure fast turn-around of the results.

The advantages of fluorescence method include a fast turn-around time, the case of fielding a portable field device, and the ability to verify a result by rerunning fluorescence or doing inductively coupled plasma atomic emission on the dissolution solution that remains unused. There are several commercial, portable fluorometers that could be used in the field. The present method from dissolution to detection could be made field portable, has a low detection limit, and can tolerate a wide variety of interferences. The method has the potential to save both man-hours and costs for the tremendous amount of beryllium analysis that is currently being done. A preferred fluorometer which is compact is USB2000 along with its standard accessories including a 380 nm light emitting diode as excitation source from Ocean Optics (Dunedin, Fla., see 2004 catalogue). This is preferably powered and/or controlled by a computer such as a laptop or a hand held computer or personal digital assistants e.g. IPAQ (from Hewlett Packard, Palo Alto, Calif.). The power may be optionally provided by a battery pack or a 12V outlet found in most vehicles.

To increase detection limit (meaning to be able to detect lower quantities of beryllium) the prior art method can be modified in several novel ways. As discussed below, one approach is to modify instrumentation and the other to modify the chemistry.

Figure 6:
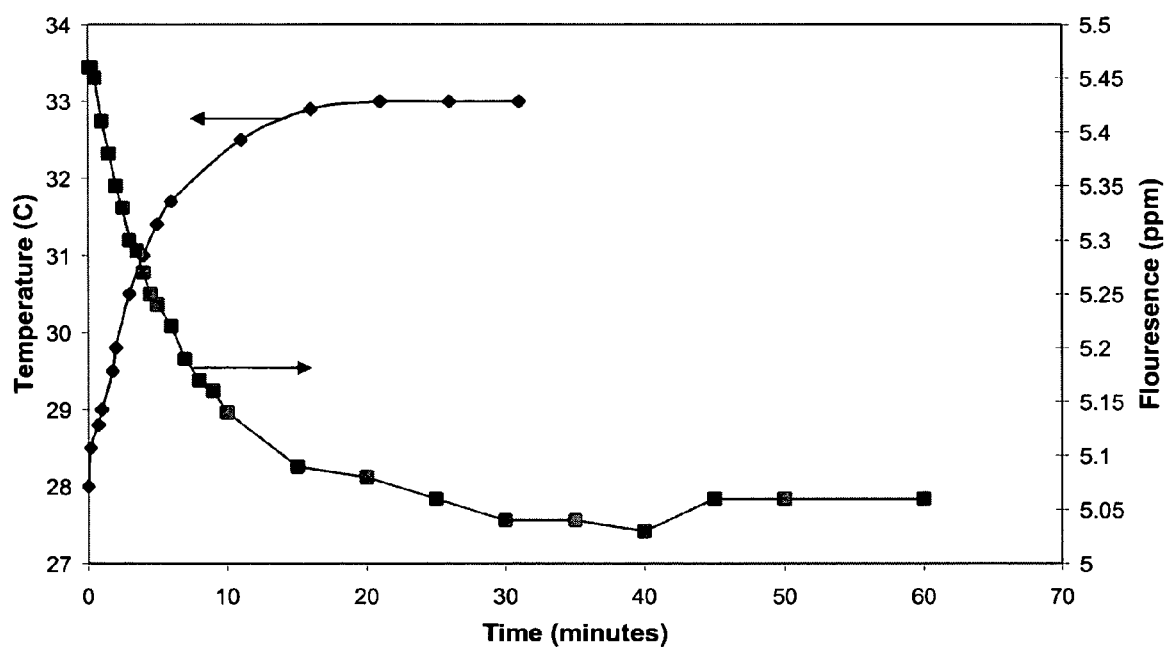
FIG. 6 Effect on fluorescence signal of a sample with changing temperature.

The sensitivity or the detection limit of this test can be easily increased by a factor of 10 or more, since the other metals do not interfere with the results and the test is specific to beryllium. The presence of other metals does not cause the background noise to increase, as is the case with other methods where the signal from decreasing quantities of beryllium is masked by the presence of other metals. To obtain high sensitivity and low noise in the measurement, it is important to control temperature of the solution (mixture of the dissolution solution and that of the detection solution also called "measurement solution") while measuring fluorescence. FIG. 6 shows the change in fluorescence with temperature. This temperature must be controlled within a narrow band as compared to the temperature at which the measurements were made on mixtures of known quantities of beryllium in the detection solution or "calibration standard solutions". In addition, a preferred range of temperature to measure fluorescence is between 10° C. and 40° C., and a more preferred range is between 10° C. and 25° C. A preferred range of temperatures where all the standards and the sample must be analyzed is within 6° C. and more preferably within 2° C. and most preferably within 1° C. This means that the temperature of all calibration solutions and the samples measured against a calibration curve from these solutions should be kept within this range during measurement. For low noise high sensitivity detection it is preferred to keep a tight control on the temperature. This may be done by increasing the airflow around the sample compartment as long as the air temperature in the room is strictly maintained. Another way is to have a constant temperature fluid circulation bath, or even having the temperature be controlled using Joule-Thompson or Peltier (or also called thermoelectric) devices in close proximity to the sample holder. Generally the thermoelectric (TEC) devices comprise of two ceramic plates that are separated by n-type and p-type semiconductor material. By applying an appropriate voltage to the semiconducting material it is possible to transfer heat from one of the ceramic plates to the other plate, thus creating a hot plate and a cold plate. Thus TEC can be used to cool or heat a device through controlling the voltage applied to the TEC. One or more of these TEC heaters (or their ceramic plates) are put in close association with the surface of the cuvet or with the sample holder which fits snugly around the cuvet. These are also integrated with thermocouples for monitoring the sample temperature (e.g. cuvet surface) and providing feedback to the temperature control mechanism.

Figure 7A:
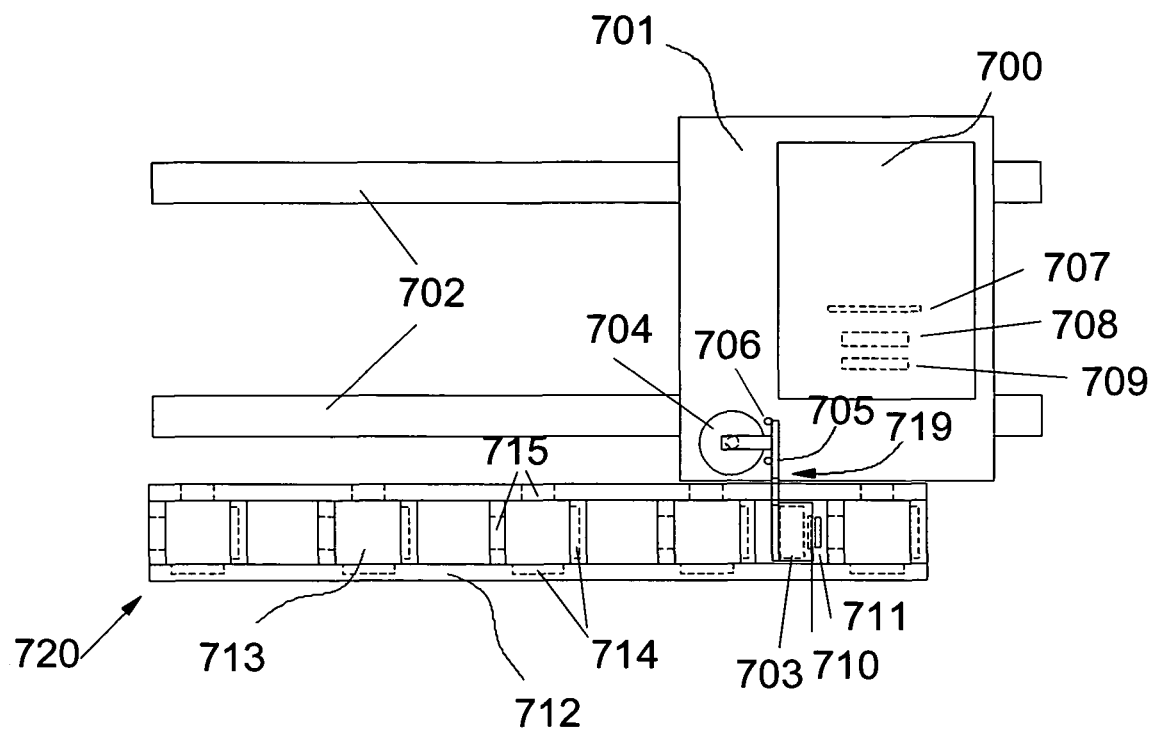
FIG. 7a: Schematics of the flurometer with high sensitivity.
Figure 7B:
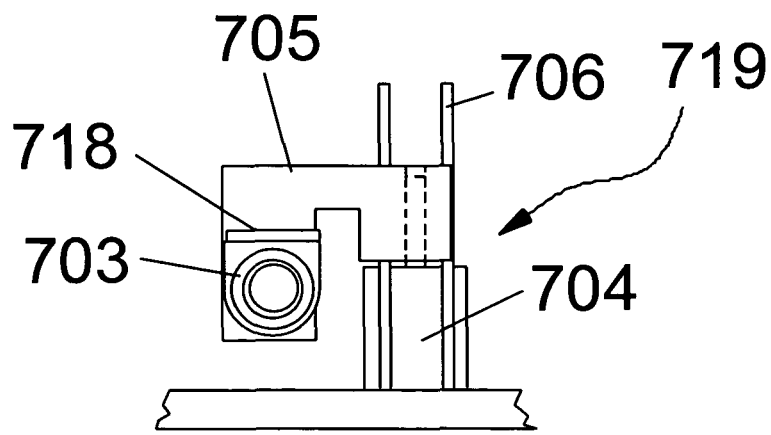
FIG. 7b: Light sensor mechanism of the fluorometer.
Figure 7C:
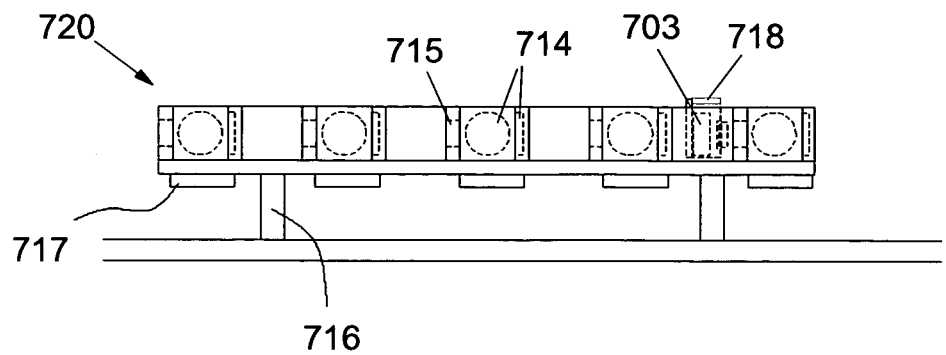
FIG. 7c: Sample holder mechanism of the fluorometer.

FIG. 7a shows a top view of one possible set-up which incorporates the improvements to increase the sensitivity of the instrument. The light source 700 (LED, tungsten lamp, etc.) is mounted on a plate carrier 701 which moves on rails 702. The carrier can be driven by a motor driven ball screw or by a pneumatic mechanism. Positioning sensors (not shown) indicate to the controller the stops for the measurements. The same carrier plate holds the light sensor mechanism 719. This mechanism comprises of a light sensor 703 and the light sensor positioning control (up and down). The mechanism 719 consists of a linear solenoid 704 rigidly attached to a plate 705 which is moved up and down on rails 706. This plate can also support any electronics serving the sensor. The up position allows the movement of the plate 701 along the cuvet holder by keeping the sensor over the holders. The down position is for measuring, positioning the light source and the sensor at the same level. The light source can also have a filter 707, a shutter 708 and a lens or system of lenses 709 to collimate the light. The sensor system includes a filter 710 and optic elements 711 to collect efficiently the fluorescent light. It can also include a shutter to protect the sensor. FIG. 7b shows the sensor mechanism 719 in more detail from another view (the numbering sequence of parts is similar to that of FIG. 7a). The sample holder mechanism is shown as 720. This mechanism comprises of metal cuvets' holder 712 which consists of pockets 713 used to hold the standards and one or more samples. The arrangement shown in the figure is linear but it can be a circular one, moving around the stationary light and sensor set. Each cuvet pocket can have mirrors 714 to improve the light collection. They can be flat or concave. Also, each pocket has openings 715 facing the source and the sensor. The construction of the holder is such that allows a good thermal conduction. FIG. 7c shows schematically a side view of the cuvet holder mechanism 720. Posts 716 keep the holder above the instruments base to allow free or forced air circulation below the holder. The figure also shows one possible arrangement of thermoelectric plates 717. Other arrangements are possible including the use of plates on the sides of the holder. One or more thermocouples (not shown) monitor the temperature of the cuvets' holder and feedback the information to the temperature controller. Other arrangements for the illumination (light source) of the sample are possible including the use of fiber optics, a movable illuminating fiber and stationary sensor, or a cuvet holder that is mobile, etc.

Figure 7D:
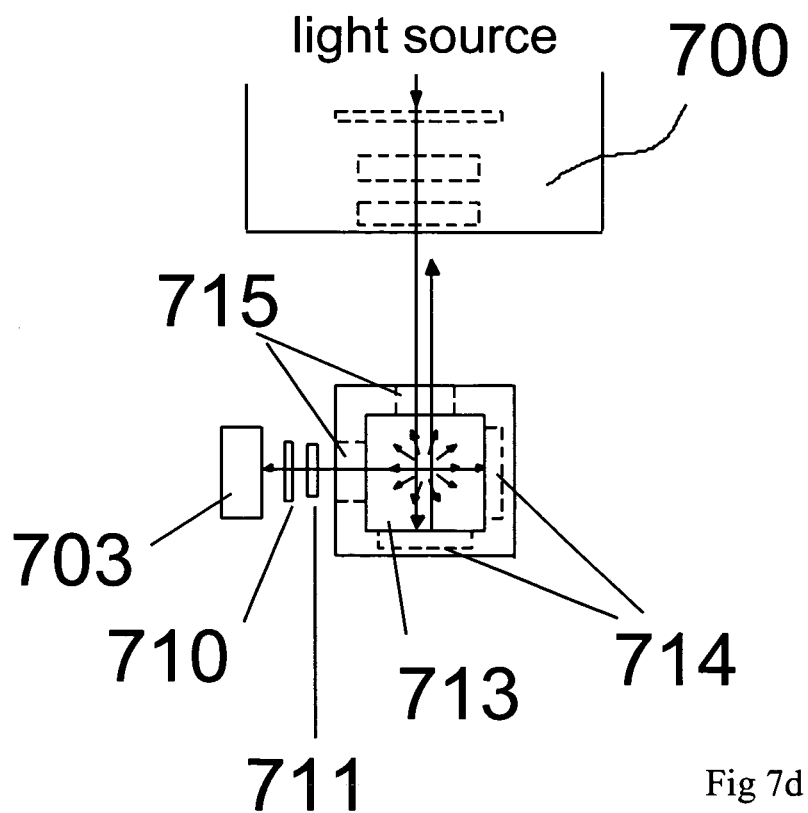
FIG. 7d: Sample along with the light detector and light source of the fluorometer.

FIG. 7d shows an expanded view of the sample cuvet 713 along with the light source 700 and a detector 703. The mirrors 714 to allow more efficient use of the incident light and also in collection of more fluorescent light.

Figure 8:
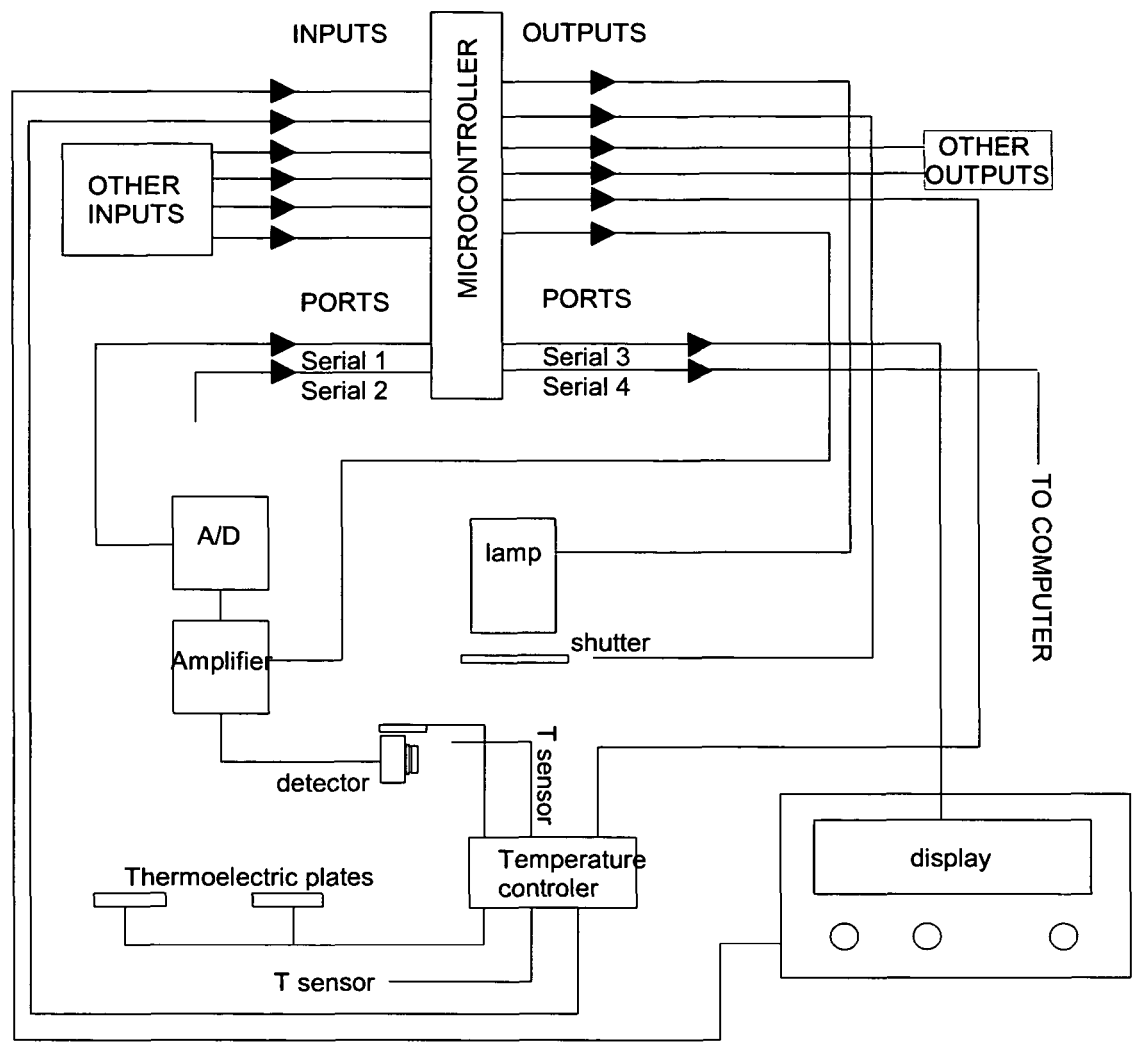
FIG. 8: Schematics of the control system for the fluorometer.

FIG. 8 shows schematically a system diagram showing the electronic control for the instrument. This comprises a microprocessor with digital and analog input/outputs and communication ports, a temperature controller and a console with a display. An example of a microcontroller is PIC 18F452 fro, Microchip Technology Inc (Chandler, Ariz.). Some examples of input to the microprocessor are console buttons, temperature sensor, slide position, detector position, lamp on and presence of sample. Similarly some of the outputs from the microcontroller are lamp on/off, shutter on/off, Detector up/down, slide control, temperature controller and gain control. Equivalently, a computer can be connected to the equipment. The temperature controller can have fixed or programmable set points. The light sensor signal is processed through an amplifier with a programmable gain and the output is converted to a digital signal sent to the microcontroller through a communications port. The measuring sequence, mathematical processing, etc. are programmed into the microcontroller.

As an example, the method may comprise of inputting a number of standards with a known concentration of the analyte. The instrument then evaluates each of these standards and fit a statistical curve through the data depending on a desired protocol. The samples to be analyzed are then individually read for fluorescence and based on the intensity detected the concentration of the analyte is calculated based on the fitted curve. The instrument may also be fitted with other statistical programs to calculate limit of detection, limit of quantification and resolution, etc.

As discussed earlier one of the most important aspect of the instrument is to exercise a good temperature control over the sample. Another important variable is the light sensor (or detector) temperature. Typically the dark current (related to the signal noise) is related to the detector temperature. A control of this at constant temperature keeps the output noise within a given range resulting in better uniformity and reproducibility. The detector temperature for all measurements should be maintained within ±5° C. and more preferably within ±1° C. Typically when the detector is maintained at colder temperatures (e.g., 20 to 100° C. below the ambient temperature), the noise is significantly reduced resulting in superior signal to noise ratio. However, it is preferred to keep cooled detectors in sealed space or purged with dry gas to avoid any condensation of moisture. As an example, avalanche photodiodes may be used as detectors. These detectors are also available where they are integrated with a thermoelectric cooling plate from Advanced Photonix (Camarillo, Calif.) with part numbers as 118-70-74-591 and 197-70-74-591, etc. Alternatively one may procure light sensors such as UDT-02UV and UDT-050UV (from UDT Sensors Inc, Hawthorne, Calif.) and put them in close contact with thermoelectric plates such as those available from Jameco electronics (Belmont, Calif.) as TE chips 172030. When the sample is irradiated by a light source the temperature increases, and this increase also depends on the length of irradiation time. Thus it is desired that the irradiation time be controlled. One way of ensuring this is to irradiate the sample only for the duration for which the data on the light sensor is collected. This period is typically called the integration time and is usually less than a minute, typically in 1 to 5 seconds range. This temperature can be controlled by providing a shutter between the light source and the sample (see 708 in FIG. 7a) which is only opened by the microcontroller when the data is being collected. Another alternative may be an LED (light emitting source) which is powered or turned on during the integration time, as long as the LED lamps reach their steady state spectral emission within a fraction of a second of being powered (preferably in less than $1/10^{th}$ of the integration time). Another way is this LED to pulsate so that any thermal load is effectively dissipated. In very sensitive measurements with short integration times the main system controller can ensure that the thermoelectric plates are not powered during the short measurement time so that temperature fluctuations can be minimized. Using light sources with low luminous energy output and detectors with high sensitivity, allows a better control over temperature of the sample and the detector due to lower amount of heating.

The detector may be a broad band photo-detector with a narrow band pass filter in front of it (see 711 in FIGS. 7a and 7d, e.g. a filter with 475 nm peak transmission with lower than ±25 nm from the peak as cut-offs) or it may be capable of measuring the entire fluorescent spectrum, from where the data at the desired wavelength is taken electronically. To have a high dynamic range and low noise a preferred A-D (Analog to Digital) converter of the light signal should have a resolution of better than 12 bits and more preferably equal or greater than 16 bits. An example of sixteen bit A-D converter is from Maxim Integrated Products Inc (Sunnyvale, Calif.) as Max 1162.

The sensor characteristics also vary with temperature. A good choice of the sensor minimizes this problem but it may still be necessary to control its temperature as well. This can be accomplished by inserting the sensor in a small metal block with a flat top to locate a thermoelectric plate 718 (FIG. 7b). The temperature of the sensor does not need to be the same as the sample in the cuvets.

One method to increase sensitivity is by having a strict temperature control during measurement as described earlier. Another way is to change chemistry so that more beryllium can be put in the "measurement solution". As described in a preferred embodiment earlier which was taken from U.S. patent application Ser. No. 10/812,444, the volumetric ratio of the dissolution solution (comprising beryllium) to the detection solution (comprising dye) was 1:19. We surprisingly found that ratios higher than 1:19 may be used to increase the detection limit of the method while keeping the other parameters constant. Increased ratios result in more beryllium in the detection solution thus increasing the sensitivity (lowering the detection of beryllium on the original media) of the method. Ratios higher than 1:12, e.g. such as 1:4 may be used to increase the beryllium content in the "measurement solution" by four times. One has to watch that the pH of the resulting "measurement solution" is still basic, preferably above 12 so as the fluorescence phenomena are not quenched. Further, the buffer capacity of the detection solution can be increased with more lysine. Since there is more beryllium in the solution, it may also require more dye in the dye solution (or detection solution) to ensure that the upper-end of the range of beryllium detection range is not compromised. If a ratio of dissolution solution to detection solution of 1:4 is used, the dye concentration may have to increase by a factor of four or five. This, which may be optionally combined with the thermal modification described above, could allow detection limits to 0.0004 µg or lower per wipe or filter media. In a test method, all samples (solutions obtained after dissoluting beryllium or its compounds from the media) may be first analyzed using solution ratio of 1:19. Since only 0.1 ml of the 5 ml solution is analyzed in the above test, the remainder of the solution may be re-tested using the high sensitivity ratio of 1:4 for those samples only which for example do not show presence of beryllium in the first analysis or those that show values of lower than 0.02 µg.

Figure 5:
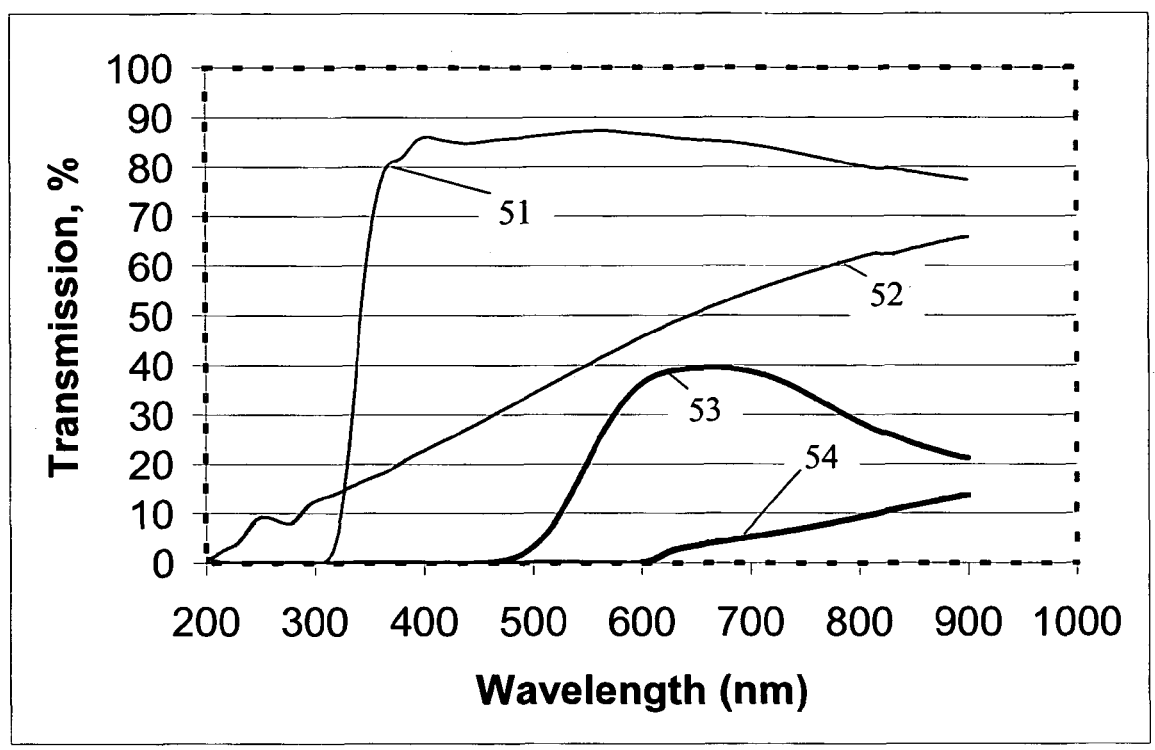
FIG. 5 Transmission spectra of containers used for storing samples of detection solution.

Aging characteristics of the solutions have to be considered for practical kits comprising these dissolution and detection solutions. The solutions should be stable to normal transportation and lab storage, preferably for a period greater than 30 days, and more preferably greater than 120 days, and most preferably greater than 180 days. The ammonium bifluoride solution may be stored in plastic (e.g., polyester, polypropylene, polycarbonate, polyethylene, etc.) or low alkaline glass bottles such as borosilicate glass. It is preferred that if soda lime glass is used, the bottles are lined with a polymeric coating. The buffered detector solution is sensitive to light. As shown in FIG. 1, this solution absorbs radiation below the wavelength of 450 nm. Thus it is preferred that this be stored and shipped in containers which transmit low amounts of radiation below 450 nm. These containers are preferably made out of a plastic as outlined for ammonium bifluoride solution or of any glass. FIG. 5 shows the transmission spectrum of walls of various plastic and glass containers. Spectra 51 is for a soda-lime clear glass bottle, spectra 52 is for a translucent (white) high density polyethylene (HDPE) bottle, 53 is for an amber colored glass bottle and 54 for a brown colored HDPE bottle. The translucent white HDPE bottle, amber bottle and the HDPE brown bottle were all purchased from Fisher Scientific (Pittsburgh, Pa.) with the respective part numbers as 03-083-39; 05-719-291 and 03-083-125. Bottles with spectra 53 and 54 are preferred as they are almost opaque below 450 nm. The bottle walls with spectra 51 and 52 allow too much of visible and/or UV radiation to pass through which may compromise the solution storage. There may be other ways to block the harmful radiation, e.g. wrapping up the more transparent containers in opaque cardboard, plastic and metal boxes or foils and films. Another preferred way is to paint/coat the bottle walls with those materials which substantially block the radiation below 450 nm. For ease of use and storage in laboratories the most preferred way is to have container walls of the bottles which will be opaque below 450 nm.

Figure 4:
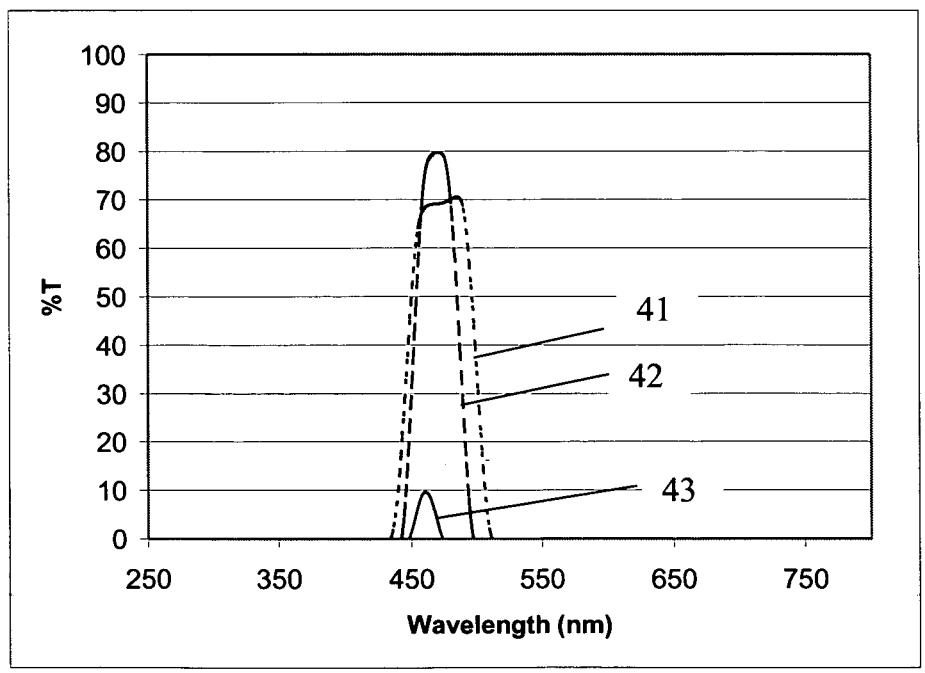
FIG. 4 Transmission spectra of typical emission filters used in fluorometer.

For fluorescence instruments the choice of emission and detection filters is important. For beryllium measurement using this chemistry, the peak (or the center of the maximum transmission peak or plateau) position should be in a range of 420 to 600 nm, more preferably between 430 to 520 nm and most preferably between 440 to 500 nm. The desired width (FWHM) of the bandpass filter is dependent on the peak position when selected from the above-mentioned range. For example with a filter with symmetrical transmission vs. wavelength characteristics around its peak, a filter with a peak transmission at 460 nm should have a preferred bandpass of less than ±20 nm, whereas, a filter with a peak transmission at 470 nm should preferably have a band pass of less than ±30 nm. For example transmission of a preferred filter peaks at 475 with a bandpass lower than ±25 nm. Optical characteristics of some of the emission filters which may be used are shown as 41, 42 and 43 in FIG. 4. Filter 43 is NB460 from Barnstead International (Dubuque, Iowa). The filter may have a flat transmission at its peak in the entire range of 440 to 500 nm, or it may have a narrow band pass only e.g., ±40 nm down to ±5 nm.

As seen in FIG. 2 the strong fluorescence is in the range of 440 to 500 nm for which the above emission filters are designed. However, one may also make use of the peak between 550 and 600 nm to measure samples with a higher amount of beryllium. To measure the higher amount of beryllium, a suitable band pass filter may be replaced in the instrument and the sample is reevaluated. Alternately, one may use a two-channel instrument where a filter for each of the range may be mounted and simultaneous measurements taken from both. Depending on the concentration of beryllium in the sample, the instrument software may decide to use one of these data to yield proper concentration. Some of the instruments which may be used for this purpose are available from Barnstead International (Dubuque, Iowa) models FM109515 and FM109535; from Turner Designs (Sunnyvale, Calif.) model numbers Aquaflor and TD700; and from Optisciences (Tyngsboro, Mass.) model GFL1. For automated system, one may use flow cells for measuring fluorescence, where solutions are automatically drawn from various solutions, individually mixing with a known quantity of the detection solution and analyzing as this mixture flows through a transparent tube (e.g. made out of quartz). The flow through cell needs to be automatically cleaned using a liquid and or gaseous media between different samples. The temperature of the tube is controlled for high reproducibility and low noise. The flow through systems are available from Agilent (Palo Alto, Calif.) and from Perkin Elmer (Boston, Mass.). Automation may also be achieved by using an auto-sampler where the standards and the unknown samples are pre-arranged in a specific fashion in a tray. The auto-sampler picks or routes these cuvets, e.g., one at a time in the fluorometer and measures these.

Example 1

Effect of Temperature

Figure 3:
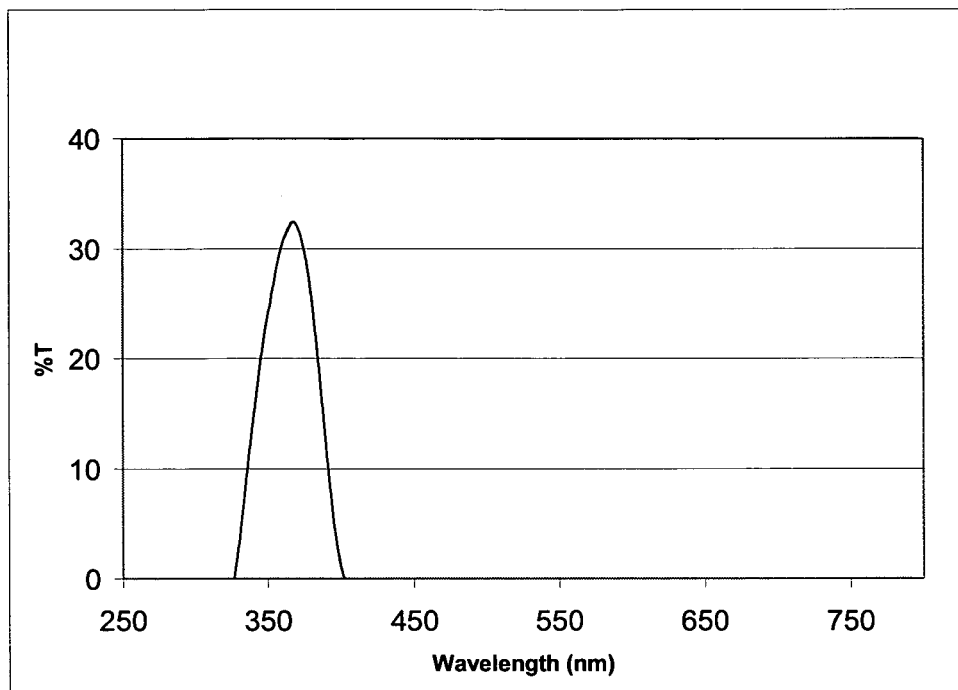
FIG. 3 Transmission spectra of a typical excitation filter used in fluorometer.

A fluorometer from Barnstead International (model FM109515) was used in this experiment. For excitation a narrow band filter (NB360 spectra is shown in FIG. 3) and for emission a narrow band filter (NB460-spectra is shown as 41 in FIG. 4) were used, both of these supplied by the instrument manufacturer. Detection solution was made by using 1.7 liters of deionized water (18 Mohms), 19.51 g of lysinemonohydrochloride, 1.99 g of EDTA disodium dihydrate, 0.0367 g of HBQS and then titrating this with a solution of 2.5N sodium hydroxide to a final pH of 12.85. 1.9 ml of the detection solution was poured in a fluorescent plastic cuvet. 0.1 ml of ammonium bifluoride solution comprising beryllium was added to the cuvet. Four different concentrations of beryllium solutions were prepared by adding 0.1 ml of 0, 2, 5 and 10 ppm standards. These were used to calibrate the fluorometer. The calibration was a straight line with a correlation coefficient of 0.99. Sample with 5 ppm sample was re-measured for fluorescence while its temperature was measured. The change in temperature occurred by leaving the sample in the fluorometer for an extended period of time and also placing the flurometer in an area where the airflow was restricted. Thus the heat was produced by the illumination lamp. FIG. 6 shows the fluorescence value measured in the fluorometer and its change in temperature. When the solution was cooled to the original temperature the fluorescence went back to the original value.

Example 2

Dissolution Solution to Detection Solution Ratio

A dissolution solution with 1% ammonium bifluoride and a detector solution were made as described in example 1. These solutions were mixed in different ratios and their pH measured. These data show that a ratio of 1:4 (dissolution solution to detection solution) still resulted in a pH in excess of 12.

| Dissolution solution (ml) | Detection solution (ml) | Volumetric ratio of "Dissolution solution:Detection solution" | pH |
|---|---|---|---|
| 0.1 | 1.9 | 1:19 | 12.46 |
| 0.4 | 1.6 | 1:4 | 12.16 |
| 0.5 | 1.5 | 1:3 | 11.39 |
| 1.0 | 1.0 | 1:1 | 8.55 |

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of determining the presence or amount of beryllium in a quantity lower than 0.02 ug in a sample, comprising:

admixing a sample suspected of containing beryllium or a beryllium compound with a dissolution solution whereby beryllium or a beryllium compound within said sample is dissolved;

mixing a portion from said admixture with a buffered solution comprising a fluorescent indicator capable of binding beryllium or a beryllium compound to the fluorescent indicator; wherein the volumetric ratio of the said admixture and the buffered solution is about 1:4, and the pH of the resulting solution is at least 12, and determining the presence or amount of beryllium or a beryllium compound within said sample by measuring fluorescence from said fluorescent indicator;

wherein the fluorescence signal is detected by passing through an optical filter which has a peak transmission in the range of 440 nm to 500 nm with a minimum bandwidth of 5 nm.

2. The method of claim 1, wherein the dissolution solution comprises at least one of ammonium bifluoride solution and an acid.

* * * * *